(12) United States Patent
Törmälä et al.

(10) Patent No.: US 6,228,111 B1
(45) Date of Patent: May 8, 2001

(54) BIODEGRADABLE IMPLANT MANUFACTURED OF POLYMER-BASED MATERIAL AND A METHOD FOR MANUFACTURING THE SAME

(75) Inventors: Pertti Törmälä ; Tero Välimaa, both of Tampere (FI)

(73) Assignee: Bionx Implants Oy, Tampere (FI)

( * ) Notice: Subject to any disclaimer, the term of this patent is extended or adjusted under 35 U.S.C. 154(b) by 0 days.

(21) Appl. No.: 09/043,633

(22) PCT Filed: Sep. 27, 1996

(86) PCT No.: PCT/FI96/00510

§ 371 Date: Aug. 7, 1998

§ 102(e) Date: Aug. 7, 1998

(87) PCT Pub. No.: WO97/11724

PCT Pub. Date: Apr. 3, 1997

(30) Foreign Application Priority Data

Sep. 27, 1995 (FI) ......................................................... 954565

(51) Int. Cl.⁷ ........................................................ A61F 2/06
(52) U.S. Cl. ...................... 623/1.38; 604/890.1; 424/426; 424/428; 623/23.75
(58) Field of Search ................................. 623/11, 1, 1.38 623/11.11; 424/426; 604/890.1

(56) References Cited

U.S. PATENT DOCUMENTS

| | | |
|---|---|---|
| 3,108,357 | 10/1963 | Liebig et al. . |
| 3,155,095 | 11/1964 | Brown . |
| 3,272,204 | 9/1966 | Artandi et al. . |
| 3,463,158 | 8/1969 | Schmitt et al. . |
| 3,620,218 | 11/1971 | Schmitt et al. . |
| 3,833,002 | 9/1974 | Palma . |
| 4,650,488 | 3/1987 | Bays et al. . |
| 4,768,507 | 9/1988 | Fischell et al. . |
| 4,923,470 | 5/1990 | Dumican . |
| 4,950,258 | 8/1990 | Kawai et al. . |
| 4,973,301 | 11/1990 | Nissenkorn . |
| 4,990,131 | 2/1991 | Dardik et al. . |
| 4,994,066 | 2/1991 | Voss . |
| 5,019,090 | 5/1991 | Pinchuk . |
| 5,061,281 | * 10/1991 | Mares et al. ............................ 623/11 |
| 5,085,629 | 2/1992 | Goldberg et al. . |
| 5,160,341 | 11/1992 | Brenneman et al. . |
| 5,326,568 | 7/1994 | Giampapa . |
| 5,697,976 | * 12/1997 | Chesterfield et al. .................. 623/11 |
| 5,741,329 | * 4/1998 | Agrawal et al. ........................ 623/11 |
| 5,769,883 | * 6/1998 | Bescemi et al. .......................... 623/1 |
| 5,919,234 | * 7/1999 | Lemperte et al. ..................... 623/16 |
| 5,948,020 | * 9/1999 | Yoon et al. ............................. 623/11 |
| 5,957,975 | * 9/1999 | Lafont et al. ............................ 623/1 |

FOREIGN PATENT DOCUMENTS

| | | |
|---|---|---|
| 0 606 165 A1 | 1/1994 | (EP) . |
| 0 578 998 | * 3/1994 | (EP) ................................ A61F/2/04 |
| WO 83/03752 | 11/1983 | (WO) . |
| WO 84/03035 | 8/1984 | (WO) . |
| WO85/03444 | 8/1985 | (WO) . |
| WO 90/04982 | 5/1990 | (WO) . |
| WO93/06792 | 4/1993 | (WO) . |
| WO 04/15583 | 7/1994 | (WO) . |

OTHER PUBLICATIONS

Daniel and Olding, Plastic. Rec. Surg. 74 (1984) 329.
Van Andersdahl et al., Seminars in Urology, vol. II (1984) 180.
Rajasubramanian et al., ASAIO Journal 40 (1994) M584.

* cited by examiner

Primary Examiner—David H. Willse
Assistant Examiner—Suzette J. Jackson
(74) Attorney, Agent, or Firm—Kenyon & Kenyon

(57) ABSTRACT

The invention relates to a biodegradable implant or the like manufactured of polymer-based material and intended to be installed in tissue conditions. In the macroscopic structure of the implant two or several zones are created in a manner that the biodegradable polymer-based material has in different zones a different detaching time from the macroscopic structure under tissue conditions.

19 Claims, 7 Drawing Sheets

(a)

(b)

(c)

(d)

BIODEGRADABLE IMPLANT MANUFACTURED OF POLYMER-BASED MATERIAL AND A METHOD FOR MANUFACTURING THE SAME

FIELD OF THE INVENTION

The invention relates to a biodegradable implant or the like manufactured of polymer-based material and intended to be installed in tissue conditions.

BACKGROUND INFORMATION

In surgery, it is known to employ biodegradable, elongated, typically tubular surgical implants and devices for supporting or combining or dividing elongated organs, tissues or parts thereof. These objects include various canals, ducts, intestines, blood vessels, tubes, such as bronchial tubes, urinary tracts, nerves etc.

In this context, the biodegradable material refers to a material manufactured of polymer, copolymer or polymer composition, the degradation and/or absorbing of which material takes place by means of metabolic reactions and/or secretion through kidneys, lungs or intestines or skin.

A multitude of publications describe various tubular implants and surgical devices manufactured of biostable or biodegradable materials. Such implants are disclosed e.g. in publications U.S. Pat. Nos. 3,108,357; 3,155,095; 3,272,204; 3,463,158; 3,620,218; WO 83/03752; WO 84/03035; Daniel and Olding, Plast. Rec. Surg. 74 (1984) 329; WO 90/04982; Van Andersdahl et al., Seminars in Urology, Vol. II (1984) 180; Raja Subra Manian, ASAIO Journal 40 (1994) M584; U.S. Pat. Nos. 4,768,507; 4,923,470; 4,973,301; 4,990,131; 4,994,066; 5,019,090; EP-0 606 165 A1; WO 04/15583; U.S. Pat. Nos. 4,950,258; 5,160,341 and 5,085,629.

Known biostable, that is, in tissues practically non-degradable implants and surgical devices of the above mentioned and corresponding type have several shortcomings. Their biostable parts, e.g. fibres, plastic and metal threads or rings or tubes or the like remain in the system even after an organ or a tissue has healed, and therefore such implants and devices can later be harmful to the patient, causing e.g. infections, inflammatory reactions, foreign body reactions and/or particles or corrosion products or the like can be released therefrom, which can further cause harmful reactions in the system.

Known biodegradable implants and surgical devices and devices of a corresponding type, e.g. of the type disclosed in the above-mentioned publications, do not cause the same kind of chronic complications as biostable implants and surgical devices, since biodegradable implants and devices absorb and degrade entirely in the system finally leaving the tissue entirely.

However, typically tubular implants and surgical devices involve the drawback that they degrade evenly at their entirely length, that is, the gradient of biodegration is directed to the centre of the cross section along the entire length of the implant or the corresponding surgical device. Thus, known elongated implants and surgical devices lose their strength evenly at their entire length, and finally the whole implant or surgical device loses its strength in a relatively short period of time at its entire length. As a result, the implant or the surgical device disintegrates evenly after having lost its strength in a short period of time or even suddenly to small pieces and particles [cf. e.g. Törmälä et al. Biomed. Mater. Res. 25 (1991) 1]. In case the disintegrating implant or surgical device is placed inside a hollow, elongated organ or tissue, it is possible that an uncontrollable quantity of particles and pieces is released from the disintegrating implant or the surgical device in a short period of time, wherein some of these parts and particles can join together and can contribute to a stoppage in the hollow tissue or organ, such as in a flow duct of a blood vessel, urinary tract or other tubular organ or tissue.

SUMMARY OF THE INVENTION

The present invention surprisingly discloses that when the implant or the corresponding surgical device is manufactured in a controlled manner to degrade so that it degrades according to its zone division, e.g. gradually starting from one end, it is possible to eliminate the danger that the prior art implants or corresponding surgical devices contribute to a stoppage in the tubular tissue or organ, and in this manner it is possible to improve the technical level in the field. A controlled degradation according to zone division provides the further advantage that the implant or the corresponding surgical device can be constructed to react in biodegradation situations exactly according to a specifically planned use.

For providing the above mentioned advantages, the implant or surgical device according to the invention is thus mainly characterized by what is presented in the characterizing portion of claim 1.

DETAILED DESCRIPTION OF THE INVENTION

An implant or a corresponding surgical device according to an advantageous embodiment of the invention has an elongated configuration and it starts to degrade in a controlled manner under tissue conditions in accordance with zone division at its first end in a manner that the implant disintegrates from said end onwards into small pieces and/or particles and/or absorbable components in a manner that degradation proceeds in a controlled manner towards the second end. Thus, small quantities of small pieces, particles and corresponding degradation products are constantly released from the implant, which pieces, particles and the like can exit the interior of the hollow organ or tissue with fluids excreted in fluid flows e.g. in urine, blood or by endocrine glands and/or due to movements of muscles surrounding the tubular tissue.

An implant or a corresponding surgical device according to the invention has advantageously an elongated configuration. It can be a tight tube or a tube perforated at its surface, a single-threaded spiral twisted of rod-like preform, a multi-threaded spiral or spiral-structured tube in which the spirals are twisted in opposite directions and pass each other above and below, forming a tubular braiding. The implant or the corresponding surgical device according to the invention can also have a configuration of a braided or knitted tube or the like. It is obvious to an expert in the field that any biostable or biodegradable elongated implant or a corresponding surgical device, e.g. those presented in the publications mentioned in the preamble of the specification, can be employed as a model when constructing implants or corresponding surgical devices in accordance with the invention.

Implants or corresponding surgical devices in accordance with the invention can be manufactured of various biodegradable polymers, copolymers or polymer alloys disclosed in abundance in the literature e.g. in publication WO 90/04982 and in Finnish patent application 953694).

Implants or corresponding surgical devices in accordance with the invention can have a non-reinforced structure, e.g.

manufactured by melt-processing techniques or solution techniques, or they can be reinforced e.g. by using self-reinforcing or reinforcing by absorbable polymeric or ceramic fibres.

Some advantageous embodiments of the implant or the corresponding surgical device of the invention are presented in the accompanying dependent claims.

The method according to the invention is mainly characterized by what is presented in the characterizing portion of the independent claim relating to the method.

The method for manufacturing an elongated implant or a corresponding surgical device is based on the fact that the macroscopic and/or microscopic structure of the implant or the corresponding surgical device is formed, according to the method, to be such that the implant or the corresponding surgical device disintegrates, according to a zone division created thereto in a controlled manner under hydrolytic conditions into small particles and/or pieces at its different parts at different times.

By regulating the macroscopic structure, the different parts of the implant or the corresponding surgical device can be disintegrated at different times by creating its walls to have different thickness at its different parts. Provided that the micro-structure of the implant or the corresponding surgical device is approximately homogeneous, usually the thinner the wall structure, the faster the disintegration. Thus, when the implant or the corresponding surgical device has a wall structure varying regularly step by step from thin to thicker, the disintegration of the implant or the corresponding surgical device takes place continuously and/or gradually from the thinner end (a first end) to the thicker end (a second end).

The microscopic structure, in its turn, can be regulated by modifying the micro-structure of the implant or the corresponding surgical device. Since the loss of strength in the implant or the corresponding surgical device is based on the hydrolysis of the polymer structure, that it, to opening of molecular bonds between the monomer units of the polymer, the implant or the corresponding surgical devices of the invention can be manufactured by providing thereto such micro-structures based on zone division which micro-structures have a different hydrolysis behaviour in different parts of the implant or the corresponding surgical device. By changing the micro-structure of the implant or the corresponding surgical device in its different parts, so that the hydrolyzation of the biodegradable material either becomes more difficult or it facilitates, it is possible to manufacture various types of biodegradable implants and corresponding surgical devices according to a zone division of the invention.

An elongated implant according to an advantageous embodiment of the method is manufactured, in order to provide zone division, to have a such geometry that the degradation speed of the implant is highest at its first end and the degrading speed is retarding when travelling from the fast-degrading end towards the slow-degrading end in the direction of the longitudinal axis of the implant. Such degradation reaction is provided e.g. by making the implant or the wall to be thicker at the second end of the implant (slower-degrading end) and thinner at the first end (faster-degrading end) in a manner that the wall thickness changes regularly or gradually from its first end to the second end in the direction of the longitudinal axis of the implant.

According to a second embodiment, the regular and/or gradual degradation according to the zone division of the implant or the corresponding surgical device is provided in a manner that the implant or the corresponding surgical device or a preform thereof is pre-hydrolyzed in a manner that the internal polymer structure of the biodegradable material is cut into pieces in a controlled manner so that the average molecular mass of the material is at its lowest value at the faster-degrading first end of the elongated implant and it increases gradually and/or step by step when travelling towards the slower-degradable second end in the longitudinal axis of the implant, in which end the molecular mass of the implant or the corresponding surgical device is at its highest value.

According to a third embodiment, since the diffusion of water into the biodegradable material is a crucial factor affecting to hydrolyzation, the implants and corresponding surgical devices of the invention can be manufactured by altering the micro-structure of the material in different parts of the implant or the corresponding surgical device in a manner that the diffusion of water into the implant or the corresponding surgical device takes place in a more difficult manner at the slowly-degradable second end than in the faster-degradable first end. Such implants or corresponding surgical devices can be manufactured e.g. of partially crystalline, biodegradable materials by manufacturing first an implant or a corresponding surgical device having an even degree of crystallinity, and then by heat treating it in a temperature gradient in a manner that the degree of crystallinity is constantly increasing in the chosen dimension of the implant, particularly in the direction of the longitudinal axis. Thus, the implant starts to degrade faster at that end (the first end) where the degree of crystallinity is lowest and degrades slower at that end where the degree of crystallinity is highest (the second end).

Further, by altering the orientation level of the biodegradable material it is possible to affect its hydrolysis reaction. Increasing the orientation level retards the diffusion of water to the biodegradable material and thus also its hydrolyzation and disintegration into pieces.

Another possible embodiment is to retard the diffusion of water to the implant or the corresponding surgical device by various coatings. If the biodegradable implant or the corresponding surgical device is coated with at least one biodegradable polymer which has poor water-permeability, by regulating the thickness of the coating layer it is possible to make the implant to degrade in different ways at its different parts in a manner that the part having the thickest coating layer degrades slowest and the part having the thinnest coating layer degrades fastest.

The invention is illustrated in the following specification, in which some examples of implants or corresponding surgical devices as well as embodiments for their manufacturing in accordance with the invention are presented with reference made to the accompanying drawings.

The invention and its functionality is illustrated by means of the following Examples which are not to restrict the scope of the invention.

EXAMPLE 1

Cylindrical, tubular implants (diameter 12 mm) were manufactured of commercial polyglycol (manufacturer: Boehringer/Ingelheim, Germany) by injection-molding technique in a manner that the implants had a conical duct inside so that at a first end of the implant the radius r1 of the duct was 5 mm, and at a second end the radius r2 was 2 mm. Thus, the thickness of the cylinder wall was 1 mm at the thinner-walled first end and 4 mm at the thicker-walled second end, and the thickness of the wall changed regularly in the entire length L=12 mm of the implant. The zone division was thus linear and continuous in the said implant.

Four implants were placed in separate baths in a phosphate-buffer solution (pH=6.1) at a temperature of 37° C., and a whirling flow state was caused in the buffer solutions by means of mechanical mixing.

Figure 2:
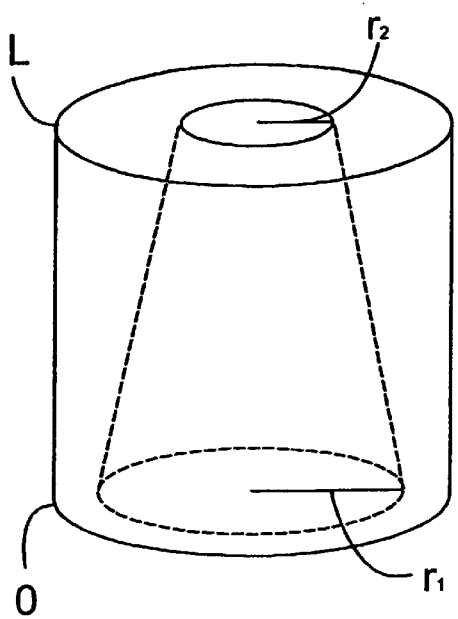
FIG. 2 shows as phases a–d a perspective-view series of the degradation of the implant according to Example 1 and FIG. 1 in a test arrangement according to Example 1.
Figure 2:
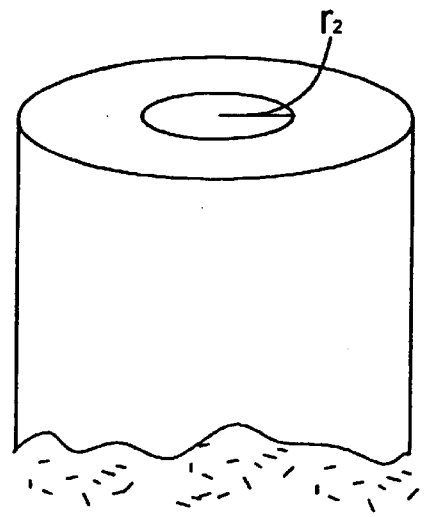
Figure 2:
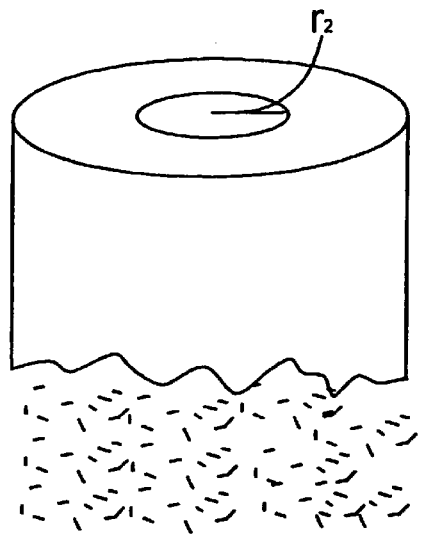
Figure 2:
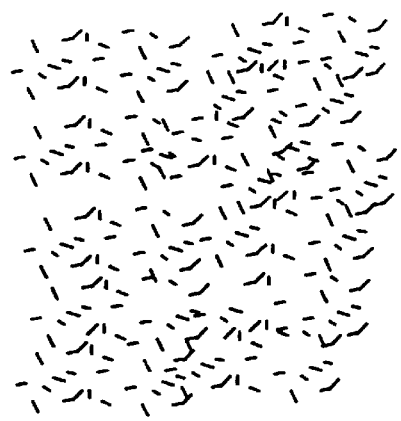

The implants were taken out of the whirling buffer solution to be examined 2, 4, 6 and 8 weeks after the hydrolysis had been started. Two weeks after the hydrolysis, there were still no changes to be seen in the implant (FIG. 2a). Four weeks after the hydrolysis, the implant had clearly started to disintegrate at the thinner wall end in a manner that the length L of the implant had become smaller with circa 2 mm and the edge of the thinner wall was coarse (FIG. 2b). Six weeks after the hydrolysis the implant had disintegrated almost to a one half of its length in the direction of the longitudinal axis L (FIG. 2c), and after eight weeks of hydrolysis the implant had totally disintegrated into the hydrolysis solution (FIG. 2d).

For providing prior art comparison material, a cylindrical blank having corresponding external dimensions as the said implant and a hole (diameter 10 mm) inside was manufactured of polyglycol. The wall thickness of this tubular blank was thus 1 mm. When hydrolysing a comparison blank of this type in a buffer solution it was noticed that two weeks after the hydrolysis the tubular blank was visually seen unaltered, but four weeks after the hydrolysis the blank had totally disintegrated into particles in the buffer solution.

By means of the above mentioned comparative tests it was demonstrated that by constructing a tubular blank (implant or a corresponding surgical device) whose wall thickness varies from thick to thin in the direction of the longitudinal axis of the blank, such a blank (implant or a corresponding surgical device) degrades step by step in a manner that the degradation is started at the thinner wall end, i.e., the gradient of the degradation is in the longitudinal direction of the implant or the corresponding surgical device.

EXAMPLE 2

There were manufactured implants having a height of 12 mm, a diameter of 12 mm and a cylindrical central hole 1 in the direction of longitudinal axis of the cylindrical configuration and with a constant diameter of 10.

Figure 1:
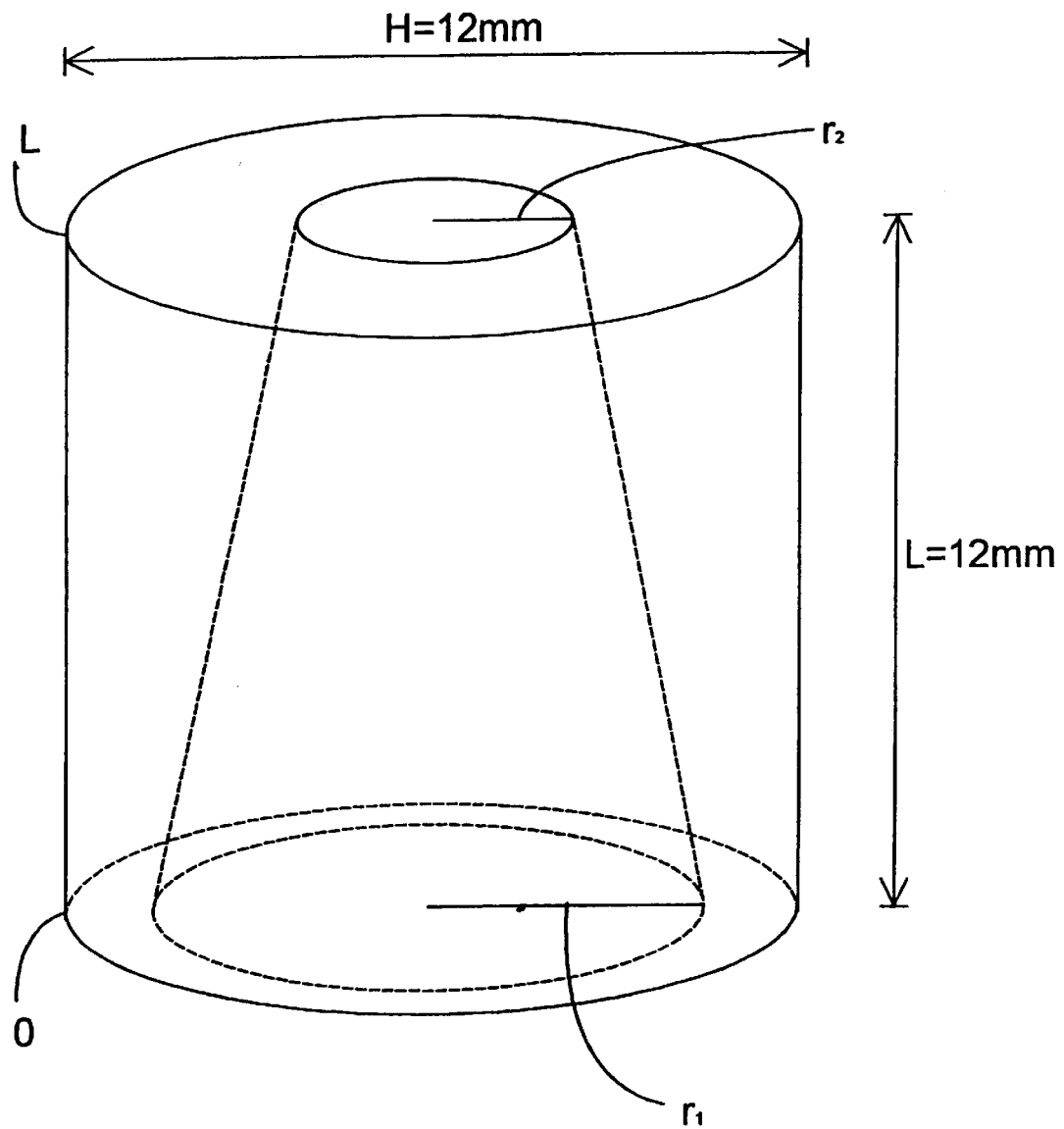
FIG. 1 shows a perspective view of an implant according to Example 1.

In the curved outer surface of the implants, there were drilled smaller radial-directed holes extending to the central hole 1 in a following manner: at the first end of the implant, close to its edge and in the direction of the periphery, around the implant holes were drilled having a diameter of 2 mm and extending to the central hole, between which holes a strip of 0.5 mm was left in the outer surface of the implant in the direction of periphery. Above this line of holes RR1 (FIG. 2), in a corresponding manner as the line of holes RR1, there were drilled other holes having a diameter of 1.5 mm having strips of 1 mm between them in a manner that between the first RR1 and the second RR2 line of holes, strips of 1 mm were left. Above the second line of holes RR2, in a corresponding manner a third line of holes RR3 was drilled, having a diameter of 1 mm and strips of 1.5 mm between them. The width of the strips between the second RR2 and the third RR3 line of holes was 1 mm. Above the third line of holes RR3, in a corresponding manner, a fourth line of holes RR4 was drilled, having a hole diameter of 0.5 mm and strips of 2 mm between the holes. The distance between the third RR3 and the fourth RR4 line of holes was 1.5 mm. FIG. 1 shows schematically an implant of the above mentioned type.

Figure 3:
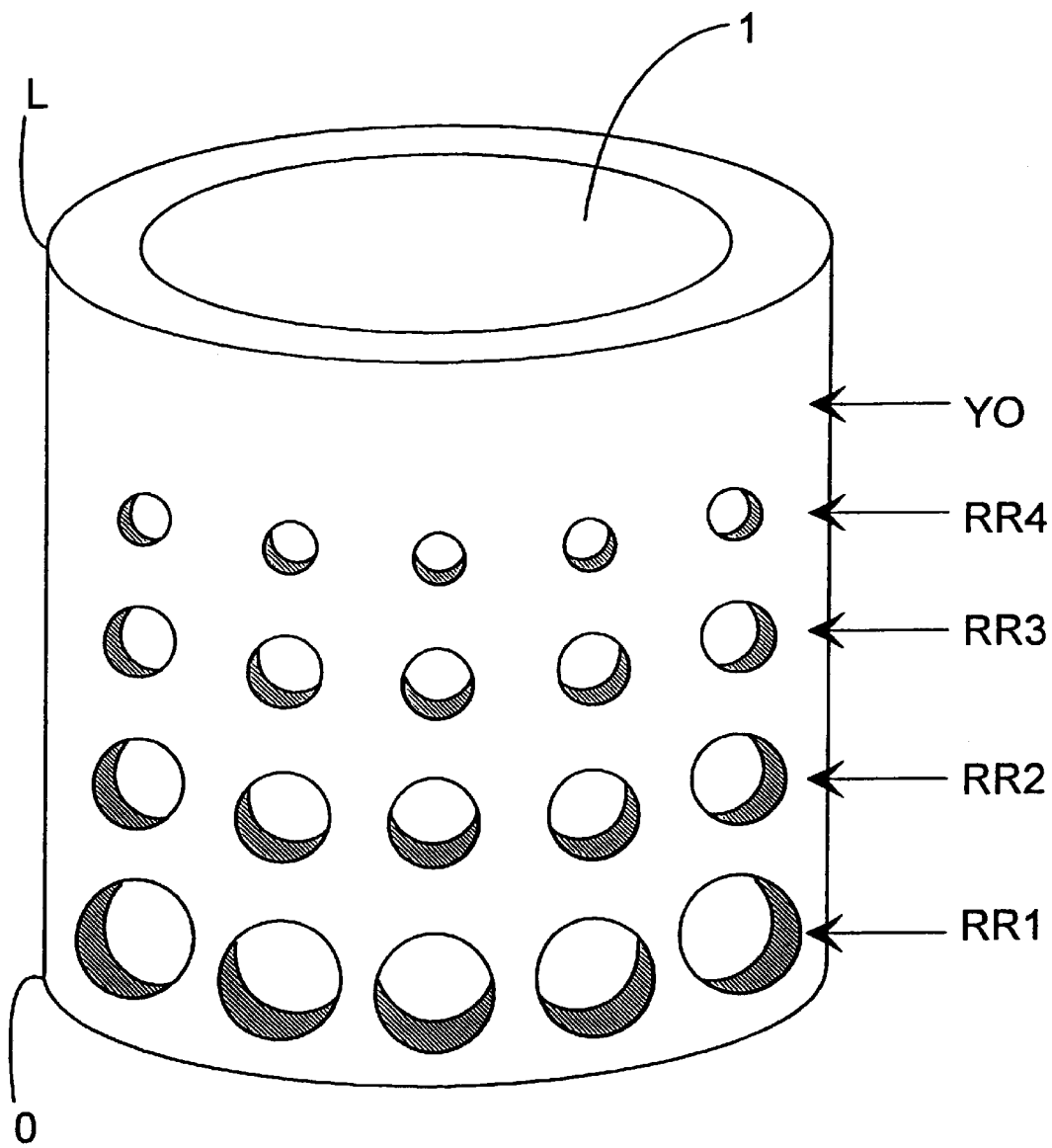
FIG. 3 shows a perspective view of an implant according to Example 2.

Implants of FIG. 3 were hydrolyzed under the hydrolysis conditions of Example 1. Implants were examined after 2, 4, 6 and 8 weeks. After two weeks of hydrolysis the implant was practically still unaltered. After four weeks of hydrolysis the test implant had totally disintegrated at the first line of holes RR1 (the first end) and partially down to the area and in the area of the second line of holes RR2. After six weeks the implant had disintegrated down to the third RR3 and fourth RR4 line of holes, but the non-drilled upper part YO (the second end) of the implant was still in one piece, although cracks and sheet erosion damages had already formed in therein. After eight weeks of hydrolysis the implant had entirely disintegrated into small particles.

EXAMPLE 3

Figure 4:
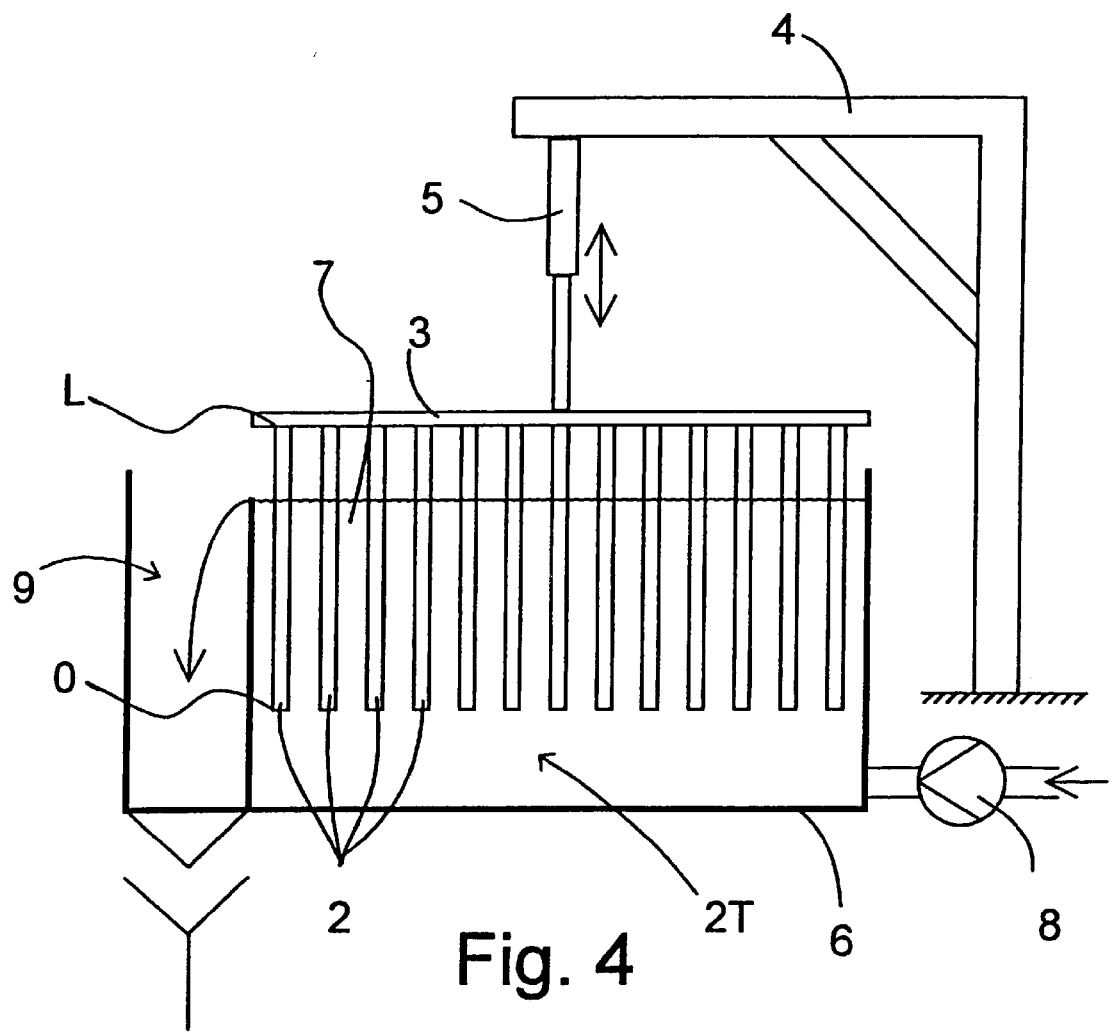
FIG. 4 shows a side view of an apparatus according to Example 3.

Preform having a width of 3 mm was manufactured by extrusion (single-screw extruder) of polyglycol according to Example 1, which preform was cooled to room temperature by means of moving cloth. Bars of 1 m were cut out of the blank. A series of bars 2 were vertically attached parallel at the same horizontal level at the second end to a chuck jaw structure 3 of a pre-hydrolysis apparatus according to FIG. 4. The chuck jaw structure 3 had been coupled to a vertical conveyor 5 in connection with a body 4, by means of which vertical conveyor it was possible to lift and lower a series of bars 2T slowly in the vertical direction. The lower ends of the series of bars 2T were thus free ("free end"). By means of the vertical conveyor 5 the bars 2 were pre-hydrolyzed in a buffer solution of Example 1 at a temperature of 37° C. by lowering them slowly in a buffer solution 7 in a tank 6, placed below the bar series 2T, by means of the vertical conveyor 5 of the chuck jaw structure 3, and by lifting them back from the solution to a room temperature by using the vertical conveyor 5. The lifting speed of the bar series 2T was 50 cm in an hour (50 cm/h), and the lifting speed of the blank was also 50 cm in an hour (50 cm/h), wherein the total term of one lift cycle was 4 hours. The series of bars 2T comprised four pieces of bars T, which were treated in hydrolysis. 40 dipping treatments were performed for the series of bars 2T. The surface of the buffer solution 7 was during the treatments at a constant height, which was maintained by a pump arrangement 8 and an overflow arrangement 9.

The pre-hydrolyzed bars 2 were dried in a vacuum at an raised temperature and they were drawn at a temperature of 160° C. to orientated blanks to a drawing ratio of 2.5, wherein orientated polyglycol blanks having a width of 0.9 mm were obtained. The blanks were wound around a heated steel tube (T=180° C.) (the outer diameter of the steel tube=8 mm) in a manner that spirals (stents) having a total length of 80 mm were obtained. The steel tubes were rapidly cooled by means of an internal air flow, wherein the spirals (stents) wound around the steel tube could be detached.

Stents were hydrolyzed 1, 2, 3 and 4 weeks in a buffer solution according to Example 1, at a temperature of 37° C., under test conditions of Example 1. The stent that had been one week in hydrolysis had started to disintegrate at its pre-hydrolyzed end. Of the stents that had been two weeks in hydrolysis, a piece of 20 mm had been disintegrated from that end which, in a preform state, had a stronger pre-hydrolysis treatment ("free end"). More than a half of the stent that had been hydrolyzed three weeks had been disintegrated, starting from the free end, and after four weeks of hydrolysis the entire pre-hydrolyzed stent had disintegrated into pieces.

For providing comparison material, stents were used which were extruded and drawn in a similar manner as the above-presented pre-hydrolyzed stents but which comparison stents were not pre-hydrolyzed. The comparison stents preserved their structure practically unaltered for 1, 2 and 3 weeks. After four weeks of hydrolysis the comparison stents were broken into several pieces and disintegrated particles had also detached from them.

EXAMPLE 4

Figure 5:
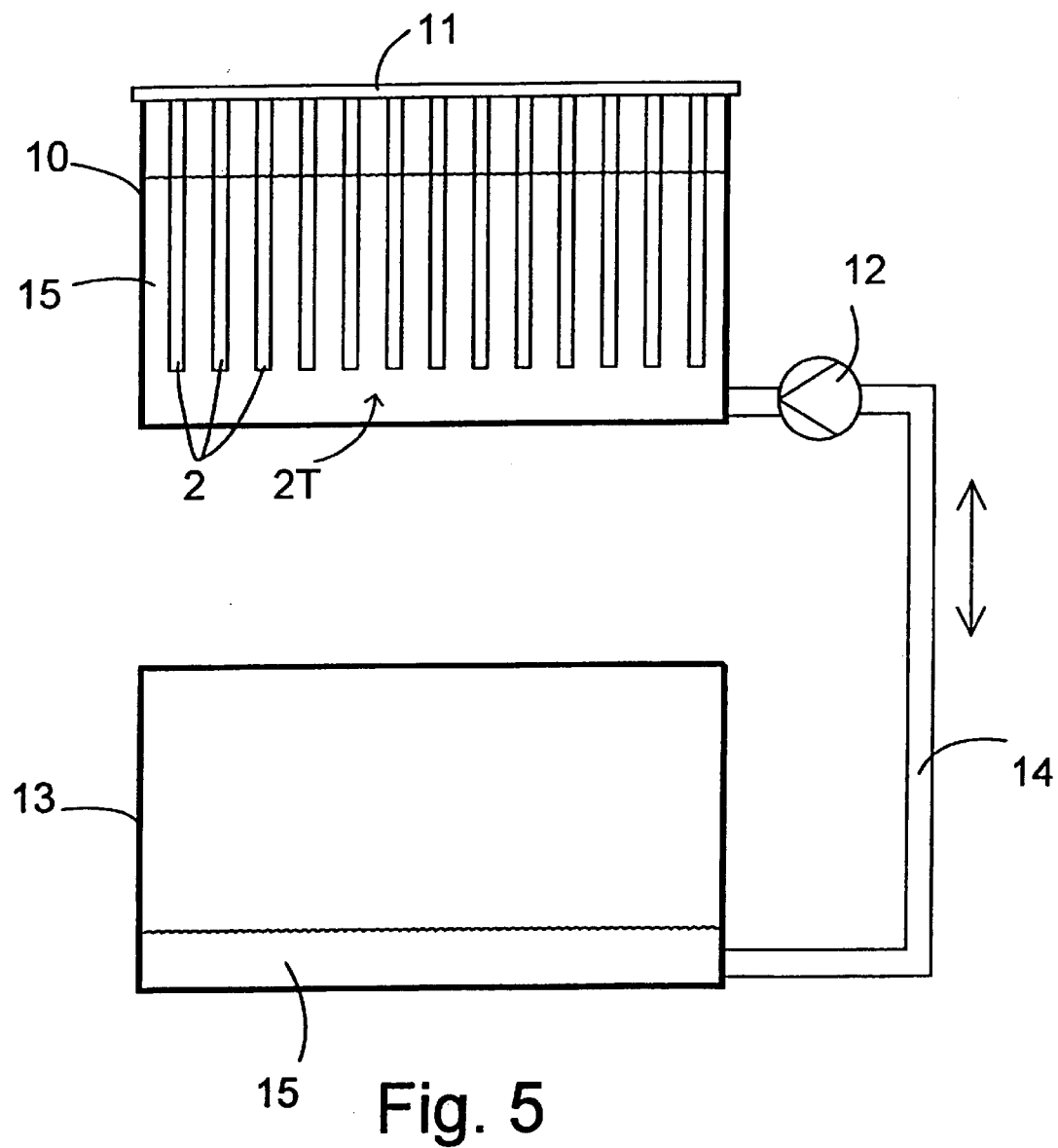
FIG. 5 shows a side view of an apparatus according to Example 4.

Cylindrical preform having a diameter of 3 mm was manufactured of amorphous (non-crystalline) lactide copolymer (Resomer, LID molecular ratio 85/15, $M_v$=200,000, manufactured Boehringen/Ingelheim, Germany) by extrusion (single-screw extruder), which preform was cooled to a room temperature on a moving cloth. A pre-hydrolysis apparatus according to FIG. 5 was created for the test arrangement. Out of the above mentioned preform, bars 2 having a length of 1 m were cut and placed as a series of bars 2T to a vertical, isolated tank 10 at a mounting bracket 11 belonging to the apparatus in a manner that the bars 2 were apart from each other in the vertical direction. By using a pump 12 in the lower part of the tank, phosphate buffer solution 15 according to Example 1 was pumped at a temperature of 70° C. slowly to the tank in a manner that the filling of the tank 10 took 10 hours. As soon as the fluid surface had risen to the level of the upper ends of the bars in the series of bars 2T, the emptying of the tanks 10 was slowly started to a reserve tank 13 through a pump 12 along the connective tube line 14. Also the emptying phase lasted 10 hours. Thus, the total length of the hydrolysis cycle was 20 hours. The pre-hydrolysis cycle for the bars was repeated 20 times.

After the pre-hydrolysis, the bars 2 to be examined were dried in a vacuum furnace at an increased temperature. Subsequently, the preforms were drawn at a temperature of 80° C. to a drawing ration of 5, wherein orientated billets having a thickness of 0.7 mm were obtained.

Figure 6:
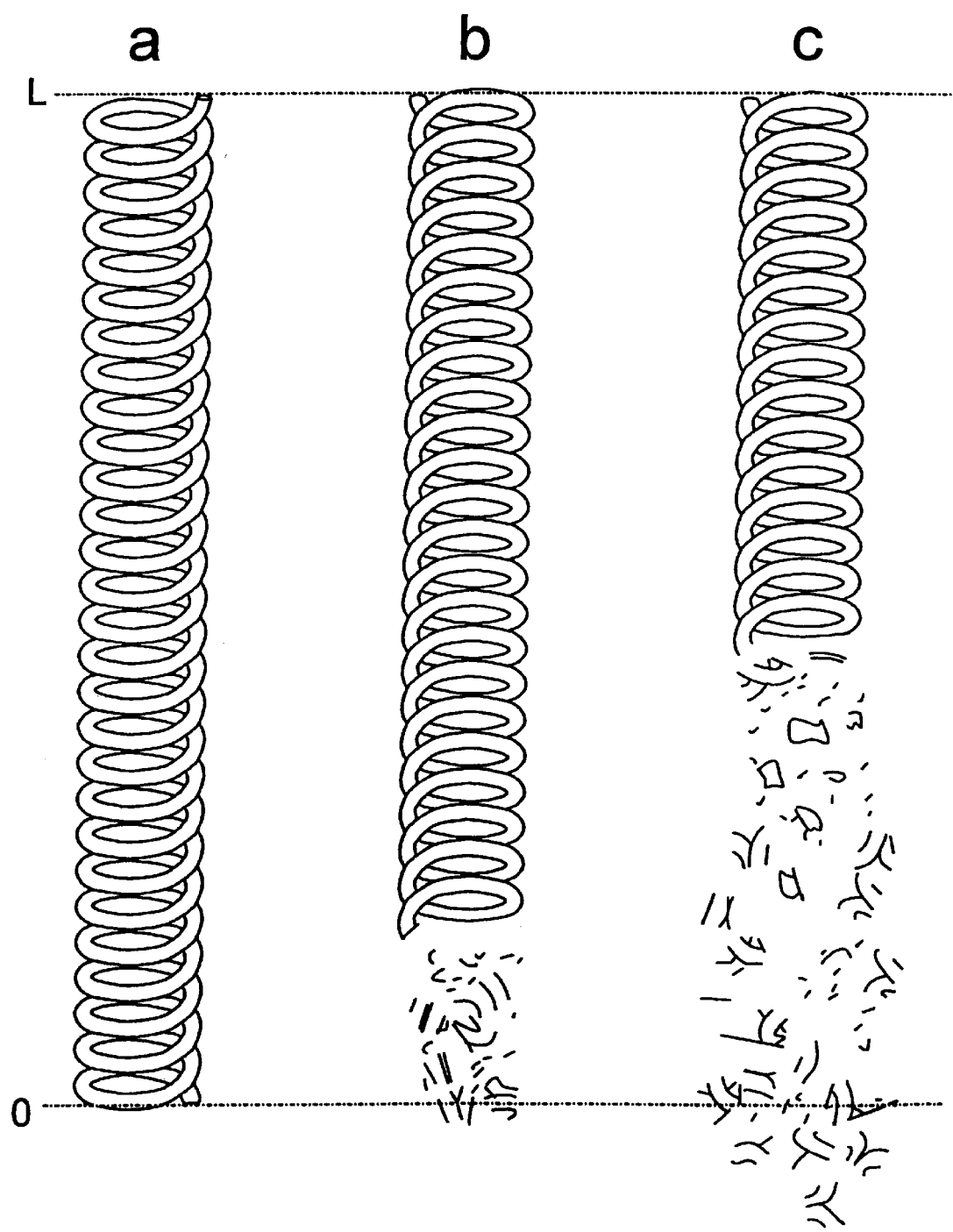
FIG. 6 shows schematically as phases a–c the degradation process in hydrolysis of the spiral test pieces, that it, stents, manufactured according to Example 4.

The billets were wound into spirals (stents) having a length of 80 mm around a heated steel tube (T=90° C.) having an outer diameter of 80 mm, the steel tube was cooled, the stent (FIG. 6a) was detached, dried in a vacuum, packed in an Al foil bag and gamma-sterilized.

Pre-hydrolyzed stent were further hydrolyzed in a buffer solution of Example 1, at a temperature of 37 C. under test conditions according to Example 1. The hydrolysis times were 15, 25 and 60 weeks. After 15 weeks of hydrolysis, a piece of the length of 1.5 cm had disintegrated into several small pieces (FIG. 6b) from the second end of the examined stent. The disintegration had taken place at that end of the stent which in the preform phase had been on the bottom of the pre-hydrolysis tank, i.e., at the end which had the strongest pre-hydrolysis treatment. After 25 weeks, approximately a half of the stent had disintegrated into pieces of various sizes (FIG. 6c) from the pre-hydrolyzed end. After 60 weeks the stent had entirely disintegrated into small pieces.

For providing comparison material, orientated and gamma-sterilized stent of a corresponding type which was not pre-hydrolyzed was used. After 15 weeks the stent was still in one piece, as it was after 25 and 40 weeks. When the hydrolysis was continued by using four parallel samples, the stents broke off at their central area or at an area close to either of the ends without any regularity after 45 to 60 weeks of hydrolysis.

A stent according to this example can advantageously be used in treatment for e.g. constrictions or retentions of the lower urinary tracts (urethra) (in the area of prostate or penile urethra) or e.g. in treatment for strictures of bile duct or pancreas duct.

EXAMPLE 5

Tube having an outer diameter of 3 mm and wall thickness of 0.7 mm was manufactured of polydioxanone sutures (PDS sutures, manufacturer: Ethicon, Germany; size 2 USP), by melting them in nitrogen atmosphere in single-screw extruder. The tube was cut into pieces of 1 m.

Pieces of the PDS-tube were attached in a vertical position on the mounting bracket in a manner that the upper ends of the PDS-tubes were left above the hydrolysis fluid. The PDS-tubes were pre-hydrolyzed by a pre-hydrolysis apparatus of Example 4 (FIG. 5) by means of a phosphate-buffer solution of 40° C. by employing a 20-hour fill-empty cycle according to Example 4. The cycle was repeated for 25 times.

The tubes were dried and they were hydrolyzed under the conditions according to Example 1 at a temperature of 37 C. After four weeks of hydrolysis, the tubes had clearly started to disintegrate at that end (lower end) which had the strongest pre-hydrolysis treatment. The upper ends of the tubes, which had been attached to the bracket, were visually seen unaltered. After six weeks of hydrolysis, over a half of the length of the tubes had disintegrated from the lower part onwards, and after eight weeks of hydrolysis the tubes were entirely disintegrated.

Corresponding non-pre-hydrolyzed tubes were used as comparison tubes. Under the test conditions of Example 1, the comparison tubes broke off into several pieces without regularity between 5 to 8 weeks.

A tube according to this example can be used as a stent e.g. between kidneys and urinary bladder in treatment of strictures or retentions of upper urinary tracts (ureter).

EXAMPLE 6

A series of tests according to Example 1 was carried out by using the following materials:

Poly-L-lactide ($M_w$ 750,000)

Glycol/trimethylene-carbonate copolymer (PGA/TMC)

Lactide/ε-caprolactone copolymer (molecular ratio 60/40, $M_w$ 100,000)

Poly-β-hydroxide-butyrate

Poly-ε-caprolactone

It was noticed that the hydrolysis tests provided corresponding results as obtained in Example 1.

EXAMPLE 7

A series of tests according to Example 2 was carried out by using the following materials:

Poly-L-lactide ($M_w$ 750,000)

Glycol/trimethylene-carbonate copolymer (PGA/TMC)

Lactide/ε-caprolactone copolymer (molecular ratio 60/40, $M_w$ 100,000)

Poly-β-hydroxide-butyrate

Poly-ε-caprolactone

The samples degraded mainly as in Example 2 in a manner that their degrading started at the end having the largest holes.

EXAMPLE 8

A series of tests according to Example 3 was carried out by using the following materials:

Poly-L-lactide ($M_w$ 750,000)

Glycol/trimethylene-carbonate copolymer (PGA/TMC)

Lactide/ε-caprolactone copolymer (molecular ratio 60/40, $M_w$ 100,000)

Poly-β-hydroxide-butyrate

Poly-ε-caprolactone

The samples degraded mainly as in Example 3 in a manner that their disintegrating started at the end that was stronger pre-hydrolyzed.

EXAMPLE 9

A series of tests according to Example 5 was carried out by using the following materials:

Poly-L-lactide ($M_w$ 750,000)

Glycol/trimethylene-carbonate copolymer (PGA/TMC)

Lactide/ε-caprolactone copolymer (molecular ratio 60/40, $M_w$ 100,000)

Poly-β-hydroxide-butyrate

Poly-ε-caprolactone

The tubular samples degraded mainly as in Example 5 in a manner that the disintegrating started at the end that was stronger pre-hydrolyzed.

EXAMPLE 10

Bar having a thickness of 3 mm was manufactured of poly-L-lactide (manufacturer: CCA Purac, Holland, $M_w$ 750,000) by single-screw extruder, which bar was cooled in air by a moving cloth. The crystalline ratio of the bar was 20% as defined by DSC-technique. A piece having a length of 20 cm was cut out of the bar and a half of it was wrapped inside a resistance tape, the temperature of which was adjusted to 120° C. The resistance tape was held around the half of bar for approximately 20 minutes, during which time post-crystallizing of the material took place. To that part of the rod which was treated with resistance tape, a crystalline ratio of 35% was obtained. The rod was placed in hydrolysis of a phosphate solution at a temperature of 37° C. (test arrangement according to Example 1), and the reactions of the rod were examined under hydrolysis conditions. After 12 months of hydrolysis the non-heat-treated (non-post-crystallized) part of the rod broke off into several pieces, whereas the post-crystallized part of the rod preserved its configuration at this phase and broke off into pieces only after 15 months of hydrolysis.

EXAMPLE 11

Cylindrical preform having a thickness of 3 mm was manufactured of poly-L/DL-lactide (L/DL-molecular ratio 70/30, incl. viscosity 5.8 dl/g, trade name RESOMER LR 708, manufacturer: Boehringer, Ingelheim, Germany) by extrusion (single-screw extruder), which preform was cooled to a room temperature. Pieces of 30 cm were cut out of the preform and a part having a length of 10 cm was turned at the centre of them to be conical in a manner that the diameter of the thicker end was 3 mm and the diameter of the thinner end was 2 mm. The preforms were drawn through a conical nozzle heated to a temperature of 70° C., which nozzle had a hole with a round cross section, the smallest diameter of the hole being 2 mm at the exit end of the conical configuration. Due to the nozzle drawing the thinner end of the conical part of the preforms remained unaltered and the thicker end was modified in a manner that its diameter altered from 3 mm to 2 mm, when the material was orientated to the drawing direction. The nozzle drawing was carried out under tension and the billets were cooled to a room temperature under tension. The billets were hydrolyzed under test conditions of Example 1 and the preservation of their configuration was examined. All the billets broke off at their non-modified part after approximately 35 weeks of hydrolysis and the disintegration proceeded as a function of time regularly towards the stronger orientated end. The final disintegration of the orientated ends of the billets took place approximately 45 weeks after the hydrolysis.

EXAMPLE 12

Self-reinforced polyglycol rods having a diameter of 2 mm were manufactured of Dexon sutures (manufacturer: Davis+Geck, England) in a hot mold by sintering in accordance with a method described in the publication P. Törmälä et al., J Biomed Mat Res., Vol. 25, (1991), p. 5. The lengths of the rods was 70 mm. The rods were coated at a second end for the length of 35 mm, by dipping the rods in a 5%-chloroform solution of polydiaxanone for several times in a manner that the dissolvent was now and then evaporated away. As a result, 50 μm thick layers of PDS were obtained on the surface of the said area in the rods. PDS-coated rods were hydrolyzed in a half of their length under hydrolysis conditions of Example 1. After two weeks of hydrolysis all the rods were in one piece. After four weeks of hydrolysis, the rods had swollen at their non-coated part and vertical cracks and breaks were formed on the surface of the non-coated part. After six weeks of hydrolysis the non-coated parts of all the rods (10 pieces) had disintegrated in the buffer solution, whereas the PDS-coated parts of the rod were whole. After ten weeks of hydrolysis also the PDS-coated parts of the rod had disintegrated.

With reference to the above presented examples the degradation of an implant manufactured according to the invention can thus be provided in the direction (longitudinal direction) of one dimension in a controlled manner by several various means. The embodiments presented in the above examples can naturally be combined; e.g. the implant of FIG. 3 can be treated with pre-hydrolysis by employing the apparatus according to FIGS. 4 or 5. Apparatus according to FIGS. 4 and 5 can be used for performing gradual pre-hydrolysis treatment in the longitudinal direction of the bars, at least in a part of the length of the bars. Also plate-like or three-dimensional pieces can be treated by means of treatment according to FIGS. 4 and 5, wherein the degradation is controlled two or three dimensionally. Correspondingly, an apparatus according to FIGS. 4 and 5 can be used for treating plates and corresponding form pieces, e.g. by combining a rotation or a corresponding movement of plates or corresponding form pieces to the relative movement between the plates and the pre-hydrolysis solution.

As to Example 2 and FIG. 3 it is to be noted that perforation RR1 . . . can also be replaced by notchings or groovings, at least partially, wherein the wall of the implant or the corresponding surgical device is not penetrated.

Figure 7:
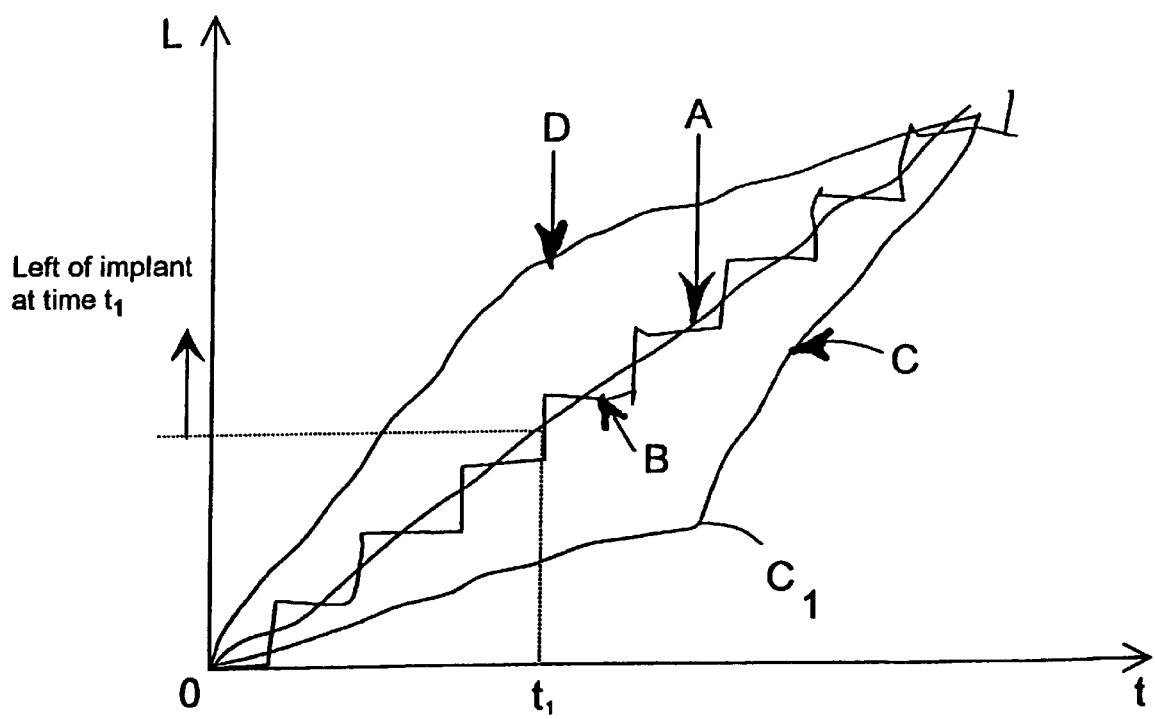
FIG. 7 shows schematically in L, t-co-ordination (the longitudinal dimension of the implant, O→,L, t=time) various degradation-time divisions provided by the method of the invention.

FIG. 7 shows schematically some degradation patterns of controlled degradation in L,t-co-ordination, where the vertical axis $0 \rightarrow L$ illustrates one dimension, e.g. length, of the implant or the corresponding surgical device, the degradation gradient being parallel with this dimension, wherein the degradation is controlled, and the horizontal axis t illustrates the time spent for hydrolysis conditions. A curve A illustrates substantially linear continuous degrading (e.g. embodiments according to FIGS. 1, 2 and 6) where mainly absorbable components and/or smaller particles are created. A curve B, in its turn, illustrates at least partially non-continuous controlled degradation e.g. according to FIG. 3, in which degradation (according to the dimensions of the strips) also particles and/or small pieces come off in addition to absorbable components. It is obvious to an expert in the field that e.g. by concentrating the pre-hydrolysis treatment in different ways in different parts of the bar it is possible to obtain a most diverse range of controlled degradation patterns, e.g. curves C and D in FIG. 7, wherein C illustrates the non-continuous point $C_1$ in the degradation process and D illustrates the accelerated degradation in the initial phase as a substantially continuous total degradation. Thus, in FIG. 7 the curves B and C are of the form $L=\Sigma f_n(t_i)$, wherein $f_n(t)$ can be any continuous function $n=1 \ldots m$ and $t_i=$a given interval $t_i \neq t$ and $t_i < t$, when L is in the area $L_i$.

The elongated implant or the corresponding surgical device is a particularly advantageous embodiment for supporting or combining or separating elongated organs, tissues or parts thereof, wherein the implant under tissue conditions starts to degrade in a controlled manner from its first end onwards in a manner that the implant degrades (disintegrates or absorbs) into small pieces and/or particles and/or absorbable components from the said end onwards, in a manner that the degradation proceeds in a controlled manner towards the second end according to zone division in a manner that different zones detach in a controlled and planned order from the macroscopic structure of the implant or the corresponding surgical device. The speed of degradation of the implant or the corresponding surgical device is highest at the first end of the implant and it retards when travelling from the fast-degrading first end towards the slow-degrading second end in the longitudinal axis of the implant. In this situation, the thickness of the wall is narrower in the fast-degrading first end than in the slow-degrading second end and/or its area/volumetric unit is larger in the fast-degrading first end than in the slow-degrading second end and/or it is pre-hydrolyzed in a manner that a stronger pre-hydrolysis is directed to the material of the implant or the corresponding surgical device in the fast-degrading first end than in the slow-degrading second end. The implant or the corresponding surgical device has an elongated configuration of a bar, tube or a spiral-structured helix or it has a structure braided or knitted of fibres.

The implant or the corresponding surgical device of the invention can also be bioactive, i.e., it can contain at least one organic or inorganic bioactive substance, such as antibiotics, chemotherapeutic agent, agent accelerating wound healing (e.g. angiogeneous growth factors), bone growth factor (bone morphogenic proteins, BMP) etc. Such bioactive implant materials are particularly advantageous in clinical use since, in addition to the mechanical effect, they have biochemical, medical and other effects for healing and ossification of organs and tissues. The bioactive substance can also be placed on the surface of the implant or the corresponding surgical device, particularly on a coating layer, e.g. mixed in a biodegradable polymer. The implant or the corresponding surgical device contains, or it can have on its surface in a special coating layer, x-ray positive (contrast) agent, such as ceramic powder (e.g. hydroxide-apatite, zirconium-oxide, calcium phosphate powder) or organic x-ray positive agent (e.g. angiographic contrast agent, such as iopamidol). By means of x-ray positive additive (contrast agent) of this type the operating surgeon is able to see the implant or the corresponding surgical during the insertion, or he can check the position of the implant or the corresponding surgical device immediately after the implantation.

It is obvious that implant materials according to the invention can further contain various additives for facilitating the processability of the material (e.g. stabilizers, antioxidants or softeners) or for altering its properties (e.g. porosifying agents, i.e., blowing agents, softeners or powder-like ceramic materials or biostable fibres, such as polyaramide or carbon fibres) or for facilitating its handling (e.g. colorants). The implant can also be manufactured of a single fiber or multiple set of fibres which are wound spirally or knitted or woven to a longitudinal tubular structure.

What is claimed is:

1. Biodegradable implant manufactured of polymer-based material and intended to be installed in tissue, comprising an elongated piece having a longitudinal axis and at least two zones of biodegradable polymer-based material, including a first zone of biodegradable polymer-based material having a first degradation time and a first detaching time in tissue and a second zone of biodegradable polymer-based material having a second degradation time and a second detaching time in tissue, wherein said first and second degradation times are different from one another and said first and second detaching times are different from one another, said longitudinal axis extending between said first zone and said second zone such that the elongated piece degrades in tissue over time along its longitudinal axis.

2. Implant as set forth in claim 1, wherein said implant is manufactured of a single fiber or multiple set of fibers which are wound spirally or knitted or woven to a longitudinal tubular structure.

3. Implant as set forth in claim 1, wherein the amount of biodegradable polymer-based material in the first zone is different than the amount of biodegradable polymer-based material in the second zone.

4. Implant as set forth in claim 1, wherein the thickness of the the biodegradable polymer-based material varies in the different zones.

5. Implant as set forth in claim 1, wherein the elongated piece contains porosity and/or holes in the zones.

6. Implant as set forth in claim 1, wherein a pre-treatment, such as pre-hydrolysis is used to being the process of degrading the elongated piece prior to its implantation in tissue.

7. Implant as set forth in claim 1, further comprising a coating of at least one biodegradable polymer on said elongated piece, wherein the coating is either pre-treated or applied on the elongated piece in a layer having varying thickness, such that the elongated piece degrades at varying rates in tissue.

8. Implant as set forth in claim 1, wherein the biodegradable polymer-based material of the first zone has a different orientation degree or crystalline degree than the biodegradable polymer-based material of the second zone.

9. Implant as set forth in claim 1, wherein the rate of detaching time in different zones in relation to other zone is a continuous time function.

10. Implant as set for in claim 1, wherein the rate of detaching time in different zones in relation to other zones is a non-continuous time function.

11. Implant as set forth in claim 1, further comprising at least one perforation, notching or the like formed in the elongated piece, wherein the size, quantity or spacing of the perforations notches or the like vary in the zones.

12. Method for manufacturing a biodegradable polymer-based implant to be installed in tissue characterized in that
the implant comprises an elongated piece having at least two zones of biodegradable polymer-based material, wherein the degradation times and the detachment times of the zones is different from each other; and
the different degradation times and detachment times for the zones is provided by a treatment directed to the biodegradable polymer-based material of the zones, including removing at least part of said material from at least one zone or modifying said material in at least one zone by forming perforations, notches or the like in said material.

13. Method as set forth in claim 12, characterized in that the biodegradable material is treated by pre-hydrolysis, wherein said pre-hydrolysis is applied in varying amounts to different zones of the elongated piece.

14. Method as set forth in claim 12, characterized in that the crystalline structure and/or orientation degree of the biodegradable material is modified.

15. Method as set forth in claim 12, characterized in that the elongated piece degrades in tissue over time along its longitudinal axis.

16. Implant as set forth in claim 1, further comprising a bioactive substance.

17. Method as set forth in claim 12, wherein the implant further comprises a bioactive substance.

18. Biodegradable implant or corresponding surgical device manufactured of polymer-based material and intended to be installed in tissue conditions, characterized in that
in the macroscopic structure of the implant two or several zones are formed in a manner that the biodegradable polymer-based material has a different disintegration time from the macroscopic structure under tissue conditions in different zones; and
in that in the longitudinal direction of the implant or the corresponding surgical device there is formed a hole having a diameter which varies in the longitudinal direction of the implant or the corresponding surgical device, wherein a perpendicular cross section against the longitudinal direction of the implant or the corresponding surgical device is constant.

19. Method for manufacturing a biodegradable polymer-based implant or a corresponding surgical device to be installed in tissue conditions, characterized in that:
the macroscopic structure of the implant or the corresponding surgical device is divided at least into two zones;
for the different zones, a treatment directed to the biodegradable material and removing the material and/or modifying its structure is performed in order to provide in different zones a different detaching time from the macroscopic structure of the implant or corresponding surgical device; and
material is removed by creating at least on hole, notch or the like in the macroscopic structure, wherein in different zones a different quantity of biodegradable material is removed.

* * * * *

UNITED STATES PATENT AND TRADEMARK OFFICE
CERTIFICATE OF CORRECTION

PATENT NO. : 6,228,111 B1
APPLICATION NO. : 09/043633
DATED : May 8, 2001
INVENTOR(S) : Tormala et al.

It is certified that error appears in the above-identified patent and that said Letters Patent is hereby corrected as shown below:

Claim 6, line 2 (column 12, line 63), "being" should be changed to --begin--; and Claim 19, line 13 (column 14, line 36), "on" should be changed to --one--.

Signed and Sealed this

Thirtieth Day of January, 2007

JON W. DUDAS
*Director of the United States Patent and Trademark Office*